(12) United States Patent
Sherman et al.

(10) Patent No.: US 7,558,707 B2
(45) Date of Patent: Jul. 7, 2009

(54) APPARATUS AND METHOD FOR INTEGRATING A PHYSICAL MOLECULAR MODEL WITH A COMPUTER-BASED VISUALIZATION AND SIMULATION MODEL

(75) Inventors: Brian H. Sherman, Belchertown, MA (US); David F. Green, Jamaica, NY (US); Karl H. Ruping, Cambridge, MA (US); Keith DeViere Donaldson, Boston, MA (US)

(73) Assignee: Molysym, Inc., Cambridge, MA (US)

( * ) Notice: Subject to any disclaimer, the term of this patent is extended or adjusted under 35 U.S.C. 154(b) by 723 days.

(21) Appl. No.: 10/750,521

(22) Filed: Dec. 31, 2003

(65) Prior Publication Data

US 2005/0004764 A1    Jan. 6, 2005

Related U.S. Application Data

(60) Provisional application No. 60/437,525, filed on Dec. 31, 2002, provisional application No. 60/477,283, filed on Jun. 10, 2003.

(51) Int. Cl.
*G06F 7/60* (2006.01)
*G06F 7/58* (2006.01)
*G09B 23/26* (2006.01)

(52) U.S. Cl. .............................. 703/2; 703/12; 434/278
(58) Field of Classification Search ...................... 703/2, 703/6, 12; 434/278
See application file for complete search history.

(56) References Cited

U.S. PATENT DOCUMENTS

RE33,785 E * 12/1991 Hildebrandt et al. ........ 434/211
5,947,745 A * 9/1999 Tempelman ................. 434/278
6,636,781 B1 * 10/2003 Shen et al. ................... 700/248

OTHER PUBLICATIONS

Accelrys, "Insight II," 8 pages, visited Dec. 30, 2003, http://www.accelrys.com/insight (document provided printed on Jan. 13, 2005).
Accelrys, "Software for Pharmaceutical, Chemical, and Materials Research," 1 page, visited Dec. 22, 2003, http://www.accelrys.com (document provided printed on Jan. 13, 2005).
Anagnostou et al., "Geometry-defining processors for engineering design and analysis," *The Visual Computer*, 5:304-315 (1989).

(Continued)

*Primary Examiner*—Paul L Rodriguez
*Assistant Examiner*—Eunhee Kim
(74) *Attorney, Agent, or Firm*—Adorno & Yoss, LLC; R. Stevan Coursey (57) ABSTRACT

Modeling systems are enhanced by combining physical and virtual modeling techniques to create a hybrid modeling system. Manipulation of physical models results in updated real-time physical characteristics being provided to a virtual model. User manipulation of virtual model characteristics can also be provided and implemented on the physical model using actuators and control devices. The invention also enables multiple users to simultaneously construct and manipulate different portions of a physical model, e.g., of an atom or a molecule, and to have the results of these manipulations provided to a computer system for computational analysis. The results of such analyses can be electronically returned to the physical model, e.g., wirelessly.

18 Claims, 6 Drawing Sheets

OTHER PUBLICATIONS

Chemistry, "WWU Virtual Molecular Model Kit," 4 pages, visited Dec. 22, 2003, http://www.chem.wwu.edu/dept/vmolckit/molecule.htm (document provided printed on Jan. 13, 2005).

Eisenberg et al., "Computationally-Enhanced Construction Kits for Children: Prototype and Principles," *Proceeding of ICLS 2003 The Fifth International Conference of the Learning Sciences*, 79-85 (2002).

Ercim News, "The Virtual Glove Box-A-New I/O Device," 2 pages, visited Dec. 22, 2003, http://www.ercim.org/publication/Ercim_News/enw46/seiler.html (document provided printed on Jan. 13, 2005).

Good, "Participatory Design of a Portable Torque-Feedback Device," *CHI*, 439-446 (1992).

Kitamura et al., "ActiveCube: A Bi-directional User Interface using Cubes," *IEEE*, 99-102 (2000).

NCSU Physics, "Molecular Model Kit," 2 pages, visited Dec. 22, 2003, http://demoroom.physics.ncsu.edu/html/demos/504.html (document provided printed on Jan. 13, 2005).

Raffle et al., "Topobo," 3 pages, visited Dec. 22, 2003, http://tangible.media.mit.edu/projects/topobo/topobo.htm (document provided printed on Jan. 13, 2005).

\* cited by examiner

FIG. 1

Node/Atom

FIG. 2A

Bond

14    Molecule

17: ↻ = rotatable bonds

18: ↱ = bendable angles

APPARATUS AND METHOD FOR INTEGRATING A PHYSICAL MOLECULAR MODEL WITH A COMPUTER-BASED VISUALIZATION AND SIMULATION MODEL

RELATED APPLICATIONS

This application claims benefit of U.S. Provisional Patent Application No. 60/437,525, filed Dec. 31, 2002, and U.S. Provisional Patent Application No. 60/477,283, filed Jun. 10, 2003.

FIELD OF INVENTION

The present invention relates generally to physical modeling and simulation and, more particularly, to an apparatus and method for interfacing a physical molecular model with a computer system for molecular visualization and simulation.

BACKGROUND

Molecular modeling generally consists of two fields: physical molecular modeling tool kits and the resulting physical models, and computer-based molecular visualization and simulation software (i.e., virtual modeling).

Physical modeling tool kits allow a person to build a physical representation, e.g., of the atomic structure of a molecule. These molecular modeling tool kits consist of hardware elements, usually spherical, that represent individual atoms and other hardware elements, usually rod-shaped, that represent bonds between atoms. Molecular modeling tool kit users can construct a physical model that demonstrates the static properties of a particular molecular structure, such as the atomic structure and the distance between atoms.

Physical modeling tool kits such as these are static and non-interactive. The resulting three-dimensional ("3-D") physical model cannot represent characteristics of the system that are not obvious to the human eye, such as the energetics of the system. Further, such models cannot represent the dynamic characteristics of the molecular system when it is in a changing environment such as shifting loads, stresses, or molecular and atomic interactions. Changing experimental variables also are not readily modeled, such as varying wind loads on a truss, bridge, or civil structure. Finally, molecular modeling tool kits and physical models do not computationally process or represent a virtual model of the subject matter on a computer screen.

Virtual software tools allow a user to create a virtual model, e.g., a molecule on a computer, to visualize the atomic structure and to simulate the characteristics of the molecular system. Examples of such commercially available software tools include Insight II, available from Accelrys (www.accelrys.com), and Virtual Molecular Dynamics (University of Chicago). Some such software tools are capable of representing the molecular structure, analyzing the molecular energetics, and simulating changes within the molecule or interactions with other molecules. Some software tools incorporate quantum mechanical effects, either by semi-empirical methods or using actual ab initio methods.

Unfortunately, although state-of-the-art visualization and simulation software is sufficiently powerful to simulate a molecular or other structure, it is difficult to obtain the geometry of choice by manipulating a virtual model on the computer screen. The user input interface in both creating the virtual model or in modifying that model for simulation is generally limited to the keyboard/mouse or a similar human-computer interface. The user can control only one parameter at a time, such as the rotation of a dihedral angle or the addition of a new atom. This process is unintuitive and time consuming.

Rather, it is more intuitive and faster to manipulate by hand a physical 3-D physical model, conforming it to the geometry of choice. However, such physical models are static and are not capable of simulating complex characteristics of the resulting structure. Even after the preferred geometry is obtained, only limited useful information can be obtained without a computer and the appropriate visualization and simulation software.

What is needed is a modeling system that includes the benefits of both physical and virtual modeling systems. Such a hybrid modeling system should include the speed and ease-of-use characteristics of physical models, and also include the advanced computational and visualization tools available in computer-based virtual modeling programs.

SUMMARY OF THE INVENTION

The present invention seeks to overcome the limitations of physical and virtual models described above by integrating them with each other. Aspects of the invention include physical models that communicate with computer-based visualization and simulation software tools, and virtual models that send information to physical models.

One aspect of the invention features a node element for use in assembling a plurality of structural elements, the node element comprising a body and one or more connection ports disposed relative to the body. At least one of the connection ports can be coupled to an adjacent structural element. The node element also includes a computational unit within the body, which receives information of physical characteristics of the node element from the connection port. The node element can also include a communications device capable of providing node element information, such as the information of the physical characteristics. The information can be used to determine a topology of the node element. The information of physical characteristics can be obtained from a sensor disposed within the node element, e.g., at or near the connection port. The information of physical characteristics from the sensors can be received by the computational unit.

Different types of sensors can be used with the node element, including sensors that detect information about at least one of movement of the node element with respect to a bond element, rotational orientation with respect to the connection port, movement of the node element with respect to one of the structural elements, position or movement of the node element with respect to an external spatial orientation reference point, and physical stress upon the node element. Sensors can include rotational sensors, accelerometers, a compass, an inclinometer, magnetometers, and gyroscopes. Some sensors can store or provide information relating to changes in the physical characteristics of the node element.

Embodiments also include the adjacent structural element comprising a bond element. Embodiments can also include a control device that manipulates a physical characteristic, e.g., the connection port. The control device can include an actuator, a vibrating unit, and/or a light emitting diode.

The node element can include a communications device that transfers data from the computational unit to one of the structural elements. A communications device of a first node element can also transfer information from a second computational unit disposed within a second node element to one of the structural elements, e.g., a structural element adjacent to the first node element. Data from a computational unit, such as information of physical characteristics of the node element, can be provided to a computer system external to the node element or the plurality of structural elements. Such data can be exchanged in both directions using the communications device, between the computational unit and the external computer system. The communications device can include a wireless transmitter, and the wireless transmitter can be used for this purpose.

Some embodiments include a node element comprising a power transmission interface, which is capable of transferring power, e.g., from a source external to the node element through at least one of the connection ports to the node element.

Another aspect of the invention features a bond element for use in assembling a plurality of structural elements, comprising a body and a first and second connection port disposed relative to the body. At least one of the connection ports can be coupled to an adjacent structural element. A computational unit is disposed within the body and receives information of physical characteristics of the bond element from the first or second connection ports. Sensors can be used to detect such information, and suitable sensors include sensors that detect information about at least one of movement of the bond element with respect to a structural element, rotational orientation with respect to the connection port, position or movement of the bond element with respect to an external spatial orientation reference point, and physical stress upon the bond element. The sensors can include rotational sensors, accelerometers, a compass, an inclinometer, magnetometers, and gyroscopes.

Yet another aspect of the invention is a hybrid modeling system comprising a physical model and a virtual model. The physical model includes at least one node element capable of being coupled to a structural element, the node element including information about physical characteristics of the node element. The virtual model runs on a computer system and the information of the physical characteristics is provided electronically from the physical model to the virtual model. The information of physical characteristics relates to a topology of the node element, and can include information relating to other structural elements of the model. The information of physical characteristics can be provided by a sensor disposed within or connected to the node element.

The modeling system can include a software program running on the computational unit and in communication with a software program running on the computer system of the virtual model. The software program of the computer system can include a graphic display visualization unit, and the visualization unit can present to a user a graphic display representing at least a portion of the physical model, at least a portion of the virtual model, or at least portions of both the physical and virtual models. The visualization unit can display structure information, energetic information, and physical properties, e.g., from the physical or virtual model of the hybrid model.

Embodiments include a communications system that provides information from the computer system of the virtual model to the computational unit of the physical model. Information can be provided to the node element from the computer system that actuates a control device disposed within or adjacent to the node element. The actuation of the control device can correspond to a virtual characteristic of the virtual model. The information can be wirelessly communicated from the computer system.

Another aspect of the invention features a structural modeling kit for use in assembling a plurality of structural elements, comprising at least one bond element and at least one node element. The bond element includes a body and a first and second connection port disposed relative to the body of the bond element. The node element includes a body and a node connection port disposed relative to the body of the node element capable of being coupled to the bond element, and a computational unit disposed within the body of the node element. The computational unit receives information of physical characteristics of the node element from the node connection port.

Node elements and bond elements of the structural modeling kit can be coupled to correspond to at least a portion of a molecular model. At least one of the node element or the bond element includes a communications device capable of providing the information of physical characteristics to an external computer system.

Yet another aspect of the invention is a method of incorporating physical information into a virtual model which comprises the step of providing a modeling system that includes a physical model that includes at least one node element capable of being coupled to a structural element, the node element comprising a computational unit including information of physical characteristics of the node element, and a virtual model that runs on a computer system. The information of physical characteristics is electronically provided from the physical model to the virtual model.

BRIEF DESCRIPTION OF THE DRAWINGS

The foregoing discussion will be understood more readily from the following detailed description of the invention, when taken in conjunction with the accompanying drawings, in which.

DETAILED DESCRIPTION

Modeling systems are used to represent, simulate, and predict the reaction of various structures within and between themselves, and generally include the coupling together of a plurality of structural elements. Such structural elements can include nodes and bonds. Bonds are commonly used to couple nodes together, and these can be used to represent, for example, molecular and atomic particles and interactions. However, similar structural modeling elements are used in many technological fields, including buildings, bridges, trusses, foundations, and many other civil structures. The invention is useful in these fields, as well as in the field of atomic and molecular modeling, and others. The invention encompasses both physical and computer-based (virtual) modeling systems. For clarity and ease of description, the following discussion and explanations focus primarily on molecular modeling technology. However, the invention has application to many other, additional, fields of endeavor.

The figures and descriptions of the present invention have been simplified to illustrate elements that are relevant for a clear understanding of the present invention while eliminating, for purposes of clarity, other elements. For example, certain system architecture details, such as certain details of the hardware and software characteristics, are not described herein. Those of ordinary skill in the art will recognize, however, that these and other elements may be desirable in a typical modeling kit, model, software system, or communications network. A discussion of such elements is not provided because such elements are known in the art and because they do not facilitate a better understanding of the present invention.

The present invention enables a user or multiple users to construct and manipulate a physical model of any molecule or molecular system and to have these manipulations be transparently transferred to a computer system for computational analysis. Different users can conveniently work on different portions of a physical model from different geographical locations, and the cumulative results of their efforts can be combined in a virtual model. Additionally, these users can simultaneously work on different aspects of a hybrid physical/virtual model while the users are located in different locations. These benefits are particularly useful for very complex models.

A limitation of previous physical and virtual modeling tools (e.g., of molecular systems) is that there is no way to physically manipulate a 3-D model in the user's hands and have those changes reflected on the computer, where more complicated molecular characteristics can be analyzed. The present invention models and simulates any molecular system including, e.g., proteins, oligonucleotides, and other biomolecular systems, in both a physical representation and a virtual representation.

Figure 1:
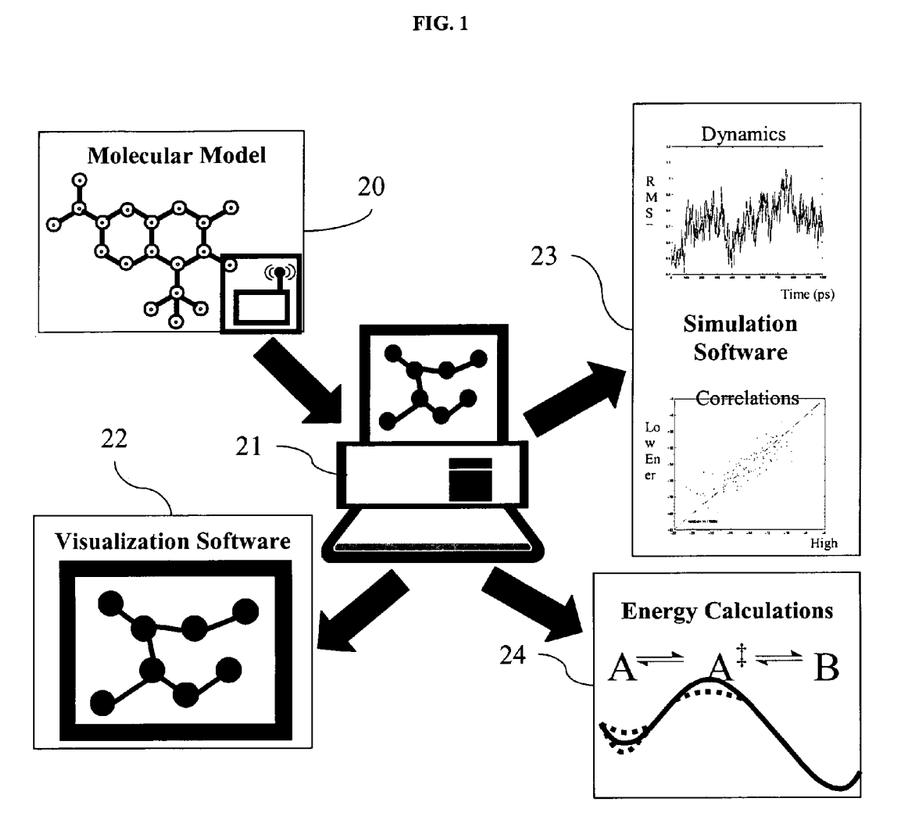
FIG. 1 is an exemplary diagram of an integrated physical model and software system for assembling, visualizing and simulating a molecular structure according to an embodiment of the present invention.

FIG. 1 is an exemplary diagram hybrid modeling system that includes an integrated physical model and software system for assembling, visualizing and simulating a molecular structure. The invention overcomes the limitations of the prior art by interconnecting a physical three-dimensional molecular model 20, constructed from a hybrid modeling system tool kit, with a computer system, such as a computer 21 with a display screen. The computer interfaces with a molecular visualization software tool 22 and a molecular simulation software tool 23. The software tools are capable of representing characteristics of a particular molecule and the changing characteristics of that molecule as it is subject to changing environments and changing molecular structures. One embodiment is an energy calculation tool 24 that updates the energy characteristics of the molecular system as the physical model is modified. Calculated variables can include Van der Walls energies, internal conformational energies (such as bonds angles, and dihedrals), screened Coulombic energies, solvation energies, and the like. Thus, the physical model can be represented in a computer-based software tool where complex calculations can be performed to determine, e.g., high-level quantum mechanical calculations, molecular dynamics, and many other types of physical characteristics. Various rendering and movie making capabilities can also be included in the software running on the computer 21.

As discussed in more detail below, the physical model 20 can include information of physical characteristics of the physical model, which can be provided from the physical model 20 to the software (i.e., the virtual model) running on the computer 21.

The physical model of the invention can be likened to an intelligent, inter-connected molecular LEGO® (Trademark of Interlego A.G. Corporation, Switzerland) set, except that molecular structures are constructed rather than toy buildings or toy robots. A user can assemble a three-dimensional model representing a molecular structure atom-by-atom. Each atomic unit can have embedded knowledge of itself, i.e., of its own state, and knowledge of the existence (or absence) of single or multiple neighboring or adjacent nodes or bonds. Some or all of these units can have a sensor and processing infrastructure that can detect and interface with other nodes or bonds, and a communication infrastructure that can detect and interface with virtual visualization and simulation software tools. Such communication can be transmitted electronically by wired, wireless, or other types of transmission systems.

The molecular modeling tool kit can also include several elements that allow for physical assembly of a model, embedded intelligence in a molecular model, and communication between atomic and molecular elements, across molecular systems, and with a computer-based software system. Following is a description of such an embodiment.

Figure 2A:
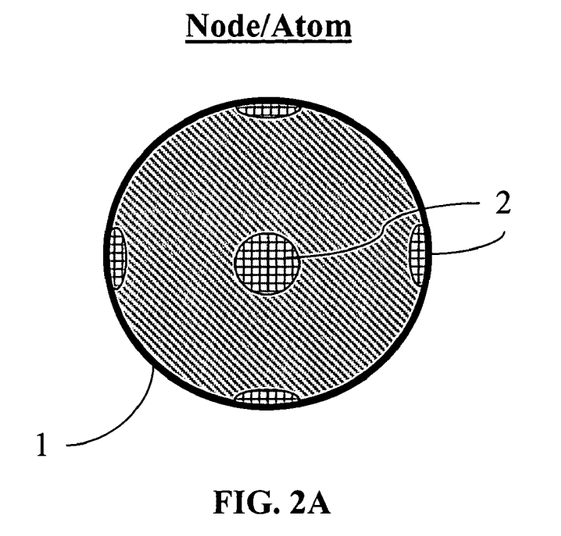
FIGS. 2A and 2B are exemplary diagrams illustrating the component parts of a molecular model comprising a node (which represents an atom) and a bond (which represents a connection between two nodes)
Figure 2B:
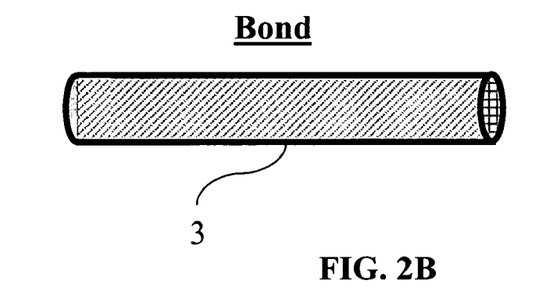

FIGS. 2A and 2B illustrate the basic component parts of a molecular model. A node element 1 can represent an atomic unit, and can be spherically shaped. Particular node elements can differ in size, color, or other characteristics according to the atom represented by that node element. The node element 1 can include one or more node connection ports 2. These can be physical connection points with other node elements, and can use bond elements 3. Particular node connection ports 2 can differ in size, color, depth, and other characteristics according to the atom or atomic bond associated with a given node connection port. A bond element 3 can represent an atomic connection or bond, and is usually rod-shaped. A bond element will generally have at least two connection ports that can be coupled to an adjacent structural element (e.g., a node element or another bond element), but it may have more than two connection ports. Bond elements can differ by size, color and other characteristics, e.g., according to the atomic bond represented by a given bond element. For example, a certain shape (e.g., square, octagonal, or triangular) can be used to differentiate a single, double, or triple bond, or a different length or color can be used to differentiate an ionic bond from a covalent bond.

Figure 3A:
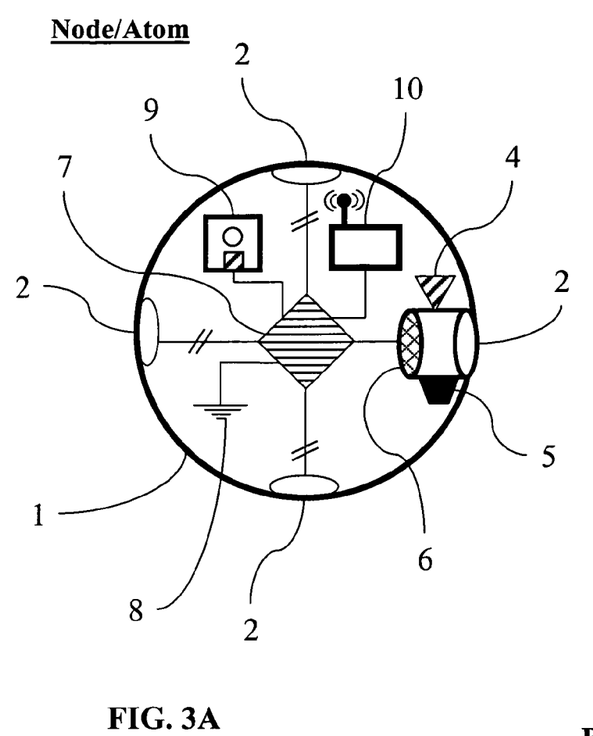
FIGS. 3A and 3B are a exemplary diagrams of the elements of the component parts of a molecular model.
Figure 3B:
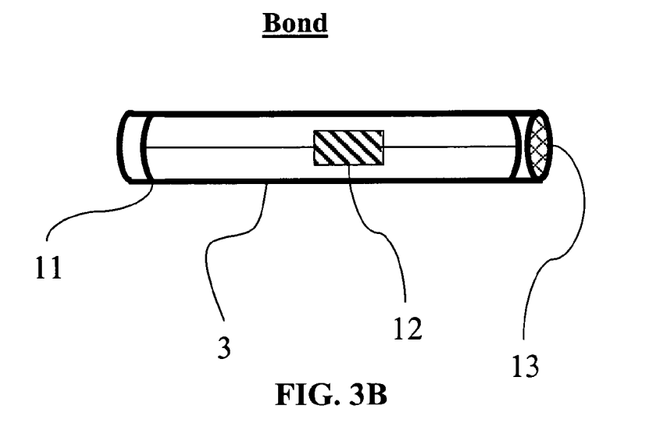

FIGS. 3A and 3B are exemplary diagrams of certain functional elements and component parts of a physical model. The node connection port 2 can be static, such as a simple hole drilled into the node element. Some embodiments include a sensor 4, a control device 5, and a communication interface 6. The sensor 4 can determine the presence (or not) of a bond element 3. Many types of sensors and sensor functions can be used, including but not limited to movement, rotation, position, stress, dynamic rotation or movement, accelerometers (to measure acceleration), a compass, inclinometers, magnetometers, and/or gyroscopes. These sensors can be used to identify information of physical characteristics of the node element, and this information can be used to determine the topology (i.e., the connection configuration and physical characteristics) of the node element. In some embodiments (not shown) two node elements can be coupled to each other without a bond element. Actuation of the control device 5 can be used to control physical characteristics of the node connection port 2, such as the degree of movement in the bond element. This actuation can be based on information provided by the virtual model, discussed in more detail below. A communication interface 6 can exchange data with other node elements 1 using the physical connection with a bond element.

The node element 1 can be used to assemble a plurality of structural elements, including other node elements and bond elements 3. The node element can be combined with an adjacent structural element, such as a bond element, to form a structural assembly corresponding to at least a portion of a physical model.

A computational device 7, such as a microprocessor, can be embedded in the node element. The computational device can be connected, wirelessly, wired, or otherwise, to an energy supply 8 (such as a battery), a memory device 9, a communications device 10, the node connection port 2, a sensor 4, and/or a control device 5. A computational unit can be used that includes both the computational device 7 and the memory device 9. The energy supply 8 can be located within a node element 1 and can supply power to the functional elements and embedded systems. Embodiments include external power sources, e.g., such that power can be transmitted to a node element through a connection port. The memory device contains the embedded rules of the physical model (e.g., an atomic unit) and operational instructions for the functioning of the node element. Such instructions can include, e.g., actuation information for control device 5. In some embodiments, the memory device can store unique characteristics of the node element 1, input data from the communications device 10, output for a transmission device, communication rules for determining the state of a physical model, basic rules for physical model building, and computational functions for the processing the instructions and interpreting the rules. The computation device 7 can control the state of the node element, i.e., interactions with connection port 2, sensor 4, control device 5, communication processes, error correction, and/or maintenance of the system.

The communication device 10 can be connected to the computational device 7 to receive or transmit data with other structural elements such as node elements or bond elements, and with the virtual model or computer-based visualization and simulation software tools running, e.g., on an external computer system. These communications can be transmitted by wire, wirelessly, or by other means known to the skilled artisan.

A bond element 3 can represent an atomic, ionic, molecular, or covalent connection or bond, and is preferably rod-shaped. Each bond element can have two bond connection ports 11, disposed at each end of the bond element. Each of these can physically couple with a node connection port 2, and can also include sensors. The types of sensors used with the node element can also be used with bond elements. In some embodiments a bond interface port 13 can facilitate communications with a node element through node connection port 2. In other embodiments the bond element 3 can include a bond communicator 12 comprising memory, computational, and communications functions. In this respect a bond communicator 12 is somewhat similar to the computational unit of the node element, and in some embodiments can perform the functions of the computational unit for a node element. The bond communicator 12 can store the identity or other characteristics (e.g., physical characteristics) of the particular bond. In some embodiments the bond element includes a physical communication capability allowing the exchange of information between the bond element and a node element, or facilitating the exchange of information between different node elements. Thus, the bond communicator 12 can perform many of the functions ascribed to the computational unit (e.g., the computational device 7) of the node element 1, thereby providing a robust, distributed, and potentially redundant computational configuration. In some embodiments the computational capability of the bond communicator is used to meet other computation requirements of the model, e.g., compensating for node elements that do not have a computational device 7.

Figure 4A:
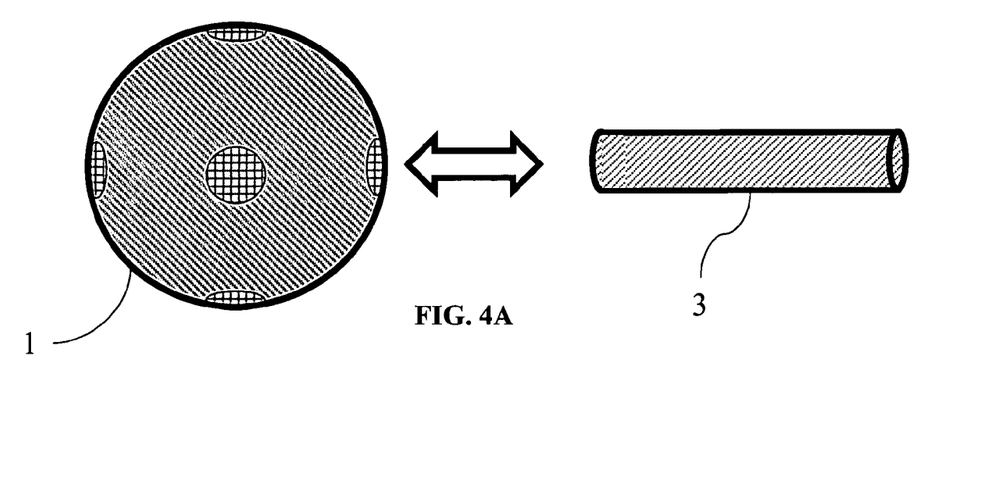
FIGS. 4A and 4B are a exemplary diagrams of the construction of a simple molecule model.
Figure 4B:
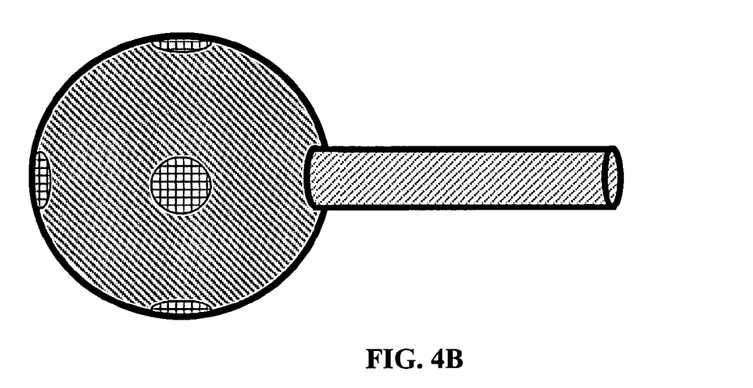
Figure 5:
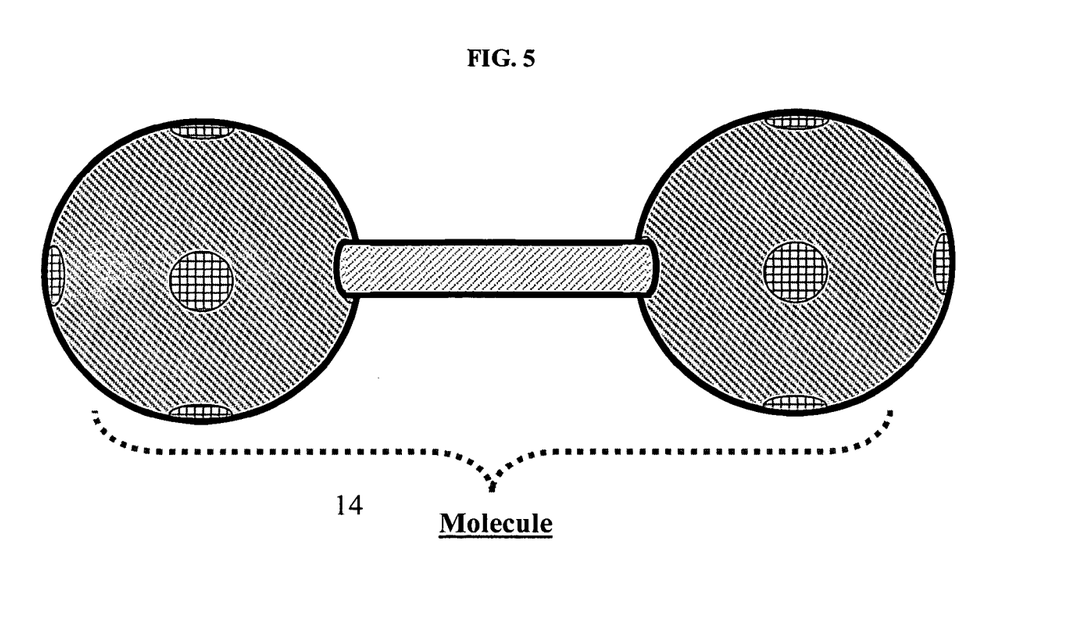
FIG. 5 is an exemplary diagram of a simple molecular model.
Figure 6:
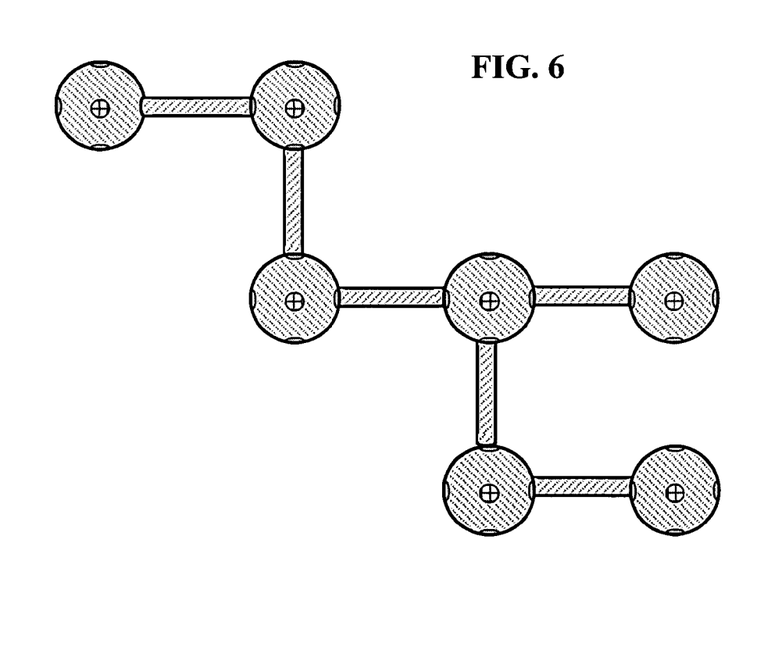
FIG. 6 is an exemplary diagram of a more complex molecular model.
Figure 7:
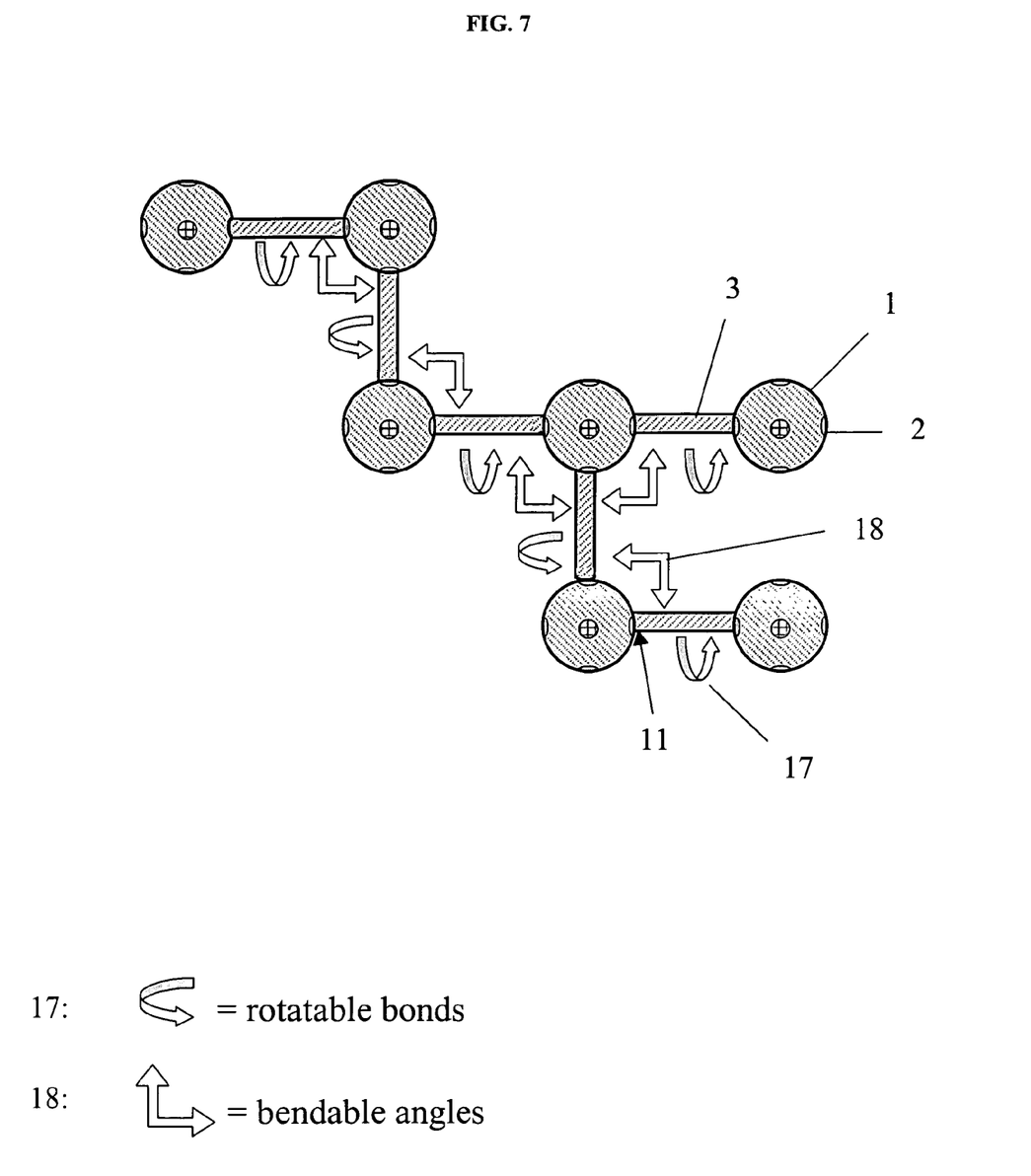
FIG. 7 illustrates some of the physical characteristics of a complex molecular model.

FIGS. 4A and 4B are exemplary diagrams illustrating the construction of a simple physical model. A node element 1 can be coupled with bond element 3, e.g., by physically connecting the parts as illustrated in FIGS. 4A and 4B. Elements and embedded devices such as these can be combined to create an intelligent physical molecular model that represents a single simple molecule 14, as illustrated in FIG. 5. With additional node elements 1 and bond elements 3, a more complex physical model can be created that represents a complex molecular structure, such as is illustrated in FIG. 6. FIG. 6 is merely a two-dimensional representation of what could be a very complex three-dimensional model. The physical characteristics of the molecular model can represent, simulate, and be used to predict, for example, physical characteristics such as the rotatable bonds 17 and the bendable angels 18 of the model, which are illustrated in FIG. 7.

In some embodiments the computation and communication requirements of a plurality of node elements of the physical model can be consolidated on to one node element that has information of constituent nodes and bonds within certain boundaries, such as within a molecule (i.e., in a molecular modeling context). In such an embodiment, use of passive elements (i.e., node or bond elements that do not include a computational unit or a bond communicator, respectively) obviates the need to install expensive computational and communication functionality in each element.

From the above it can be understood that many different embodiments of a physical model can be assembled from individual structural elements such as node elements and bond elements. The assembled structure possesses certain physical characteristics imparted to it at least in part by its physical configuration, some of which are detected and stored by the sensors 4 and other functional elements of the model. Information of these physical characteristics can then be transmitted to a virtual model, such as a simulation software tool operating on a computer 21, by means of a wired, wireless or other communications system(s).

The information of physical characteristics of the physical model is preferably provided to a virtual model operating on a computer system. Physical models created with node and bond elements, e.g., representing atomic units with imbedded knowledge and interconnectivity, can be manipulated in three-dimensional space in real time. The information thus created can be provided to a computer system external to the physical model, whereby complex calculations, predictions, and various computationally intensive modeling results can be generated and used.

The virtual modeling software can consist of visualization tools and simulation tools. A visualization software tool allows representation of the various characteristics of the physical model on a visualization platform, such as a computer screen. A simulation software tool can be used to represent and convey additional characteristics such as energetics, quantum mechanical effects, vibrational modes, crystal lattice construction, molecular dynamics and other characteristics not visible to the human eye. The simulation software tools also allow for the control or calculation of such characteristics by means of parameters or inputs supplied by the physical model, various software tools, the user, and/or various testing devices.

A user can modify input variables of the virtual model, display parameters of the molecular structure, and even create a movie of all or part of the molecular structure, or its simulation, with the click of a button. Various rendering options can also be used to create pictures of various sizes and resolutions. Such images can be posted on the Internet, or they can be of sufficient resolution to create a large poster.

FIG. 1, discussed above, illustrates a communications device 10 used to exchange information between the physical model and the virtual model of the computer-based software tool. The communications device 10 can provide the connectivity required by the hybrid modeling system, and is capable of transmitting the basic molecular geometry of the physical model to the virtual model, of the virtual model to the physical model, or both. In a preferred embodiment, such communications are performed wirelessly between one or more node elements 1 of the physical model and a peripheral communications device such as an 802.11B wireless port of a computer system (not shown). The information provided to the virtual model allows a set of molecular coordinates to be determined and displayed on a display device, such as a computer screen. Using this information, a simulation software tool can represent molecular characteristics such as energetics, quantum mechanical effects, vibrational modes, crystal lattice construction, and molecular dynamics and other characteristics not visible to the human eye. The user can also impose certain changes or restrictions through the software tools that can be displayed visually or represented in the physical model.

Moreover, embodiments include providing information of virtual characteristics from the virtual model to the physical model, such that physical characteristics are created or actuated on the physical model. Such characteristics can be represented, e.g., by LED's, vibrating units, or other suitable means. Such communications can be bi-directional. For example, physical actuation of an LED, a vibrating unit, switches, and the like on the physical model can be associated with desired virtual characteristics of the virtual model. Of course, a user can also modify the virtual model by adding or removing node element 1 (e.g., atoms) in the physical model. Manipulation of connections, rotational orientations, dihedral angles, and the like can also be used to modify attributes of the virtual model, by physically changing the physical model. In a preferred embodiment, such modifications and changes to the physical model can be updated in the virtual model in real-time. Thus, as the user modifies the physical model, those results are relayed to the virtual model where they are displayed, and can be used as input for a modeling software tool.

Characteristics of the physical model (e.g., physical characteristics) and characteristics of the virtual model (e.g., virtual characteristics) thus become somewhat intertwined using the hybrid model of the invention. An LED or some other type of display device can be used to represent on the physical model a virtual characteristic from the virtual model that would ordinarily not easily be physically displayed or be a part of a physical model. The converse relationship can also be established, wherein a device on a structural element of the physical model can be provided or manipulated by a user to represent a virtual characteristic, and information of or from this physical representation can be provided to the virtual model for computational or graphical display purposes. Distinctions between physical characteristics and virtual characteristics thus become blurred. Accordingly, if desired, each of the physical and virtual characteristics described herein can be represented in some form on the physical model, and can also be represented within and by the virtual model. In addition to physical characteristics and virtual characteristics described elsewhere in this document, such characteristics can also include positional information, relative and absolute movement of model elements (e.g., structural elements), physical pressure and/or stress on and within the model elements, the size of a node element (e.g., an atom) or a bond element such that the larger node element (e.g., carbon) is distinguished from the smaller node element (e.g., hydrogen), or a bond element representing a certain strength or type (e.g., a single bond) can be distinguished from a bond element of a different strength or type (e.g., a double bond).

When the computer-based virtual model is used to communicate with the physical model (e.g., when the invention is used as a molecular model), certain molecular rules can be imposed on the construction, or physical response, of the physical model through the software tools that reside in the computer system of the virtual model, the computational unit of the node element, and/or the bond communicator of the bond elements. Thus, a mechanism can be established that exchanges information from the physical model to the virtual model as it is visualized or simulated in the computer. Further, certain rules and new parameters can be imposed on the embedded atomic elements, such that the models can be modified as knowledge of molecular characteristics advances. In situations where experimental modeling results are desired, this process can be iterative.

Other embodiments include a feedback loop, where information is exchanged in both directions between the physical model and the virtual model. For example, when a control device 5 implements on the physical model the results of experimental virtual modeling, a user can modify or update the physical model. Such manipulation can then be detected by the physical model, as described above, and information of the updated physical characteristics can be provided to the virtual model. Another iteration of the modeling results can then be performed. This method provides to the user the benefits of both physical and virtual models and modeling techniques, while increasing efficiency and productivity.

Embodiments include a communications interface that can determine the relative location of node elements in three-dimensional space, e.g., through use of a GPS system that utilizes a position indicator, such as a beacon, at the center or on the surface of a the node element. A sensor can be provided that triangulates the position of the position indicator relative to other node elements.

The physical modeling tool and the virtual modeling tool, combined with the use of other software tools, can be used independently of each other at particular times, but can later be interconnected with each other. For example, a person can visit a potential customer with a physical model, and later upload information from the physical model to the customer's visualization or simulation software, thereby demonstrating certain characteristics that would not be obvious to the unaided human eye or intellect simply by observing the physical model.

The invention can also be used in both the classroom and research laboratory environments. For example, high school students currently using static, unintelligent models can use the invention to learn about the dynamic characteristics of physical (e.g., molecular) structures. Commercial researchers can use the invention to gain meaningful insights into the complex relationships on the atomic level, and to represent such relationships in both physical and virtual formats.

It should be understood that the invention is not limited by the foregoing description, but embraces possible such alterations, modifications, and variations.

By the above it can be seen that a highly useful apparatus and methods have been developed for creating and interconnecting various physical and virtual models, whereby considerable time savings and efficiency improvements can be obtained. The terms and expressions employed herein are used as terms of description and not of limitation, and there is no intention, in the use of such terms and expressions, of excluding any equivalents of the features shown and described or portions thereof, but it is recognized that various modifications are possible within the scope of the invention claimed.

What is claimed is:

1. A molecular modeling system for use in assembling a plurality of structural elements comprising:
   a node element comprising:
     a body;
     at least one connection port disposed relative to the body and configured to be coupled to an adjacent structural element;
     a computational unit disposed within the body configured to receive information of physical characteristics of the node element from the connection port; the computational unit including:
       a memory device for storing embedded rules of the body and operational instructions associated with functioning of the node element, the instructions including:
         unique characteristics of the node element,
         input data from a communications device,
         output data from a transmission device,
         communication rules for determining a state of the body,
         rules for building the body, and
         computational functions for processing of the instructions and interpreting the communication rules and the rules for building; and
       the communications device capable of providing data from the computational unit to an external computer system; and
   a bond element comprising:
     a body;
     a first and a second connection port disposed relative to the body, at least one of the first and the second connection ports capable of being coupled to the node element; and
     a computational unit disposed within the body, wherein the computational unit receives information of physical characteristics of the bond element from at least one of the first and second connection ports.

2. The molecular modeling system of claim 1, wherein the communications device is capable of providing node element information.

3. The molecular modeling system of claim 1, wherein the adjacent structural element comprises a bond element.

4. The molecular modeling system of claim 1, wherein the computational unit of the node element uses the information of physical characteristics to determine a topology of the node element.

5. The molecular modeling system of claim 4, wherein the information of physical characteristics is obtained from a sensor disposed within the node element.

6. The molecular modeling system of claim 5, wherein the sensor detects information about at least one of movement of the node element with respect to a bond element, rotational orientation with respect to the connection port, movement of the node element with respect to one of the structural elements, at least one of a position and a movement of the node element with respect to an external spatial orientation reference point, and physical stress upon the node element.

7. The molecular modeling system of claim 6, wherein the sensor comprises at least one of a rotational sensor, an accelerometer, a compass, an inclinometer, a magnetometer, and a gyroscope.

8. The molecular modeling system of claim 6, wherein the sensor is configured to store and provide information associated with changes in physical characteristics of the node element.

9. The molecular modeling system of claim 1, wherein the node element further comprises a control device that manipulates a physical characteristic of the connection port.

10. The molecular modeling system of claim 9 wherein the control device comprises at least one from a set of an actuator, a vibrating unit, and a light emitting diode.

11. The molecular modeling system of claim 2, wherein the communications device is configured to transfer data from the computational unit to one of the structural elements.

12. The molecular modeling system of claim 1, wherein the communications device exchanges information between the external computer system and the computational unit.

13. The molecular modeling system of claim 1, wherein the node element further comprises a power transmission interface capable of transferring power from an external source through at least one of the connection ports and to the node element.

14. The molecular modeling system node element of claim 1, wherein the communications device comprises a wireless transmitter.

15. A molecular modeling system for use in assembling a plurality of structural elements comprising:
   a bond element comprising:
     a body;
     a first and a second connection port disposed relative to the body, at least one of the first and the second connection ports capable of being coupled to an adjacent structural element;
     a computational unit disposed within the body, wherein the computational unit receives information of physical characteristics of the bond element from one of the first and second connection ports; and
     a communications device capable of providing data from the computational unit to other structural elements; and
   a node element comprising:
     a body;
     at least one connection port disposed relative to the body, at least one connection port capable of being coupled to the bond element; and
     a computational unit disposed within the body, configured to receive information of physical characteristics of the node element from the connection port, the computational unit including:
       a computational device; and
       a memory device for storing embedded rules of the body and operational instructions for functioning of the node element, the instructions including:
         unique characteristics of the node element,
         input data from a communications device,
         output data from a transmission device,
         communication rules for determining state of the body,
         rules for building the body, and
         computational functions for processing of the instructions and interpreting the communication rules and rules for building.

16. The molecular modeling system of claim 15, wherein the bond element further comprises a sensor that detects information about at least one of movement of the bond element with respect to a structural element, rotational orientation with respect to the connection port, a position of the bond element, and a movement of the bond element with respect to an external spatial orientation reference point, and physical stress upon the bond element.

17. The molecular modeling system of claim 16, wherein the sensor comprises at least one of a rotational sensor, an accelerometer, a compass, an inclinometer, a magnetometer, and a gyroscope.

18. A structural modeling kit for use in assembling a plurality of structural elements comprising:
   a plurality of bond elements, each bond element comprising:
      a body; and
      a first and a second connection port disposed relative to the body of the bond element; and
   a plurality of node elements, each node element comprising:
      a body;
      a node connection port disposed relative to the body of the node element, capable of being coupled to the bond element; and
      a computational unit disposed within the body of the node element, wherein the computational unit receives information of physical characteristics of the node element from the node connection port; wherein at least one of the node elements and the bond elements comprises a communications device capable of providing the information of physical characteristics to an external computer system; wherein at least one node element and at least one bond element are coupled to correspond to at least a portion of a molecular model; and wherein the computational unit including:
         a computational device; and
         a memory device for storing embedded rules of the body and operational instructions for functioning of the node element, the instructions including:
            unique characteristics of the node element,
            input data from a communications device,
            output data from a transmission device,
            communication rules for determining state of the body,
            rules for building the body, and
            computational functions for processing of the instructions and interpreting the communication rules and rules for building.

\* \* \* \* \*